Oct. 14, 1952 H. L. MARKEN ET AL Plant Pat. 1,138
RAPHIOLEPIS PLANT
Filed Sept. 10, 1951
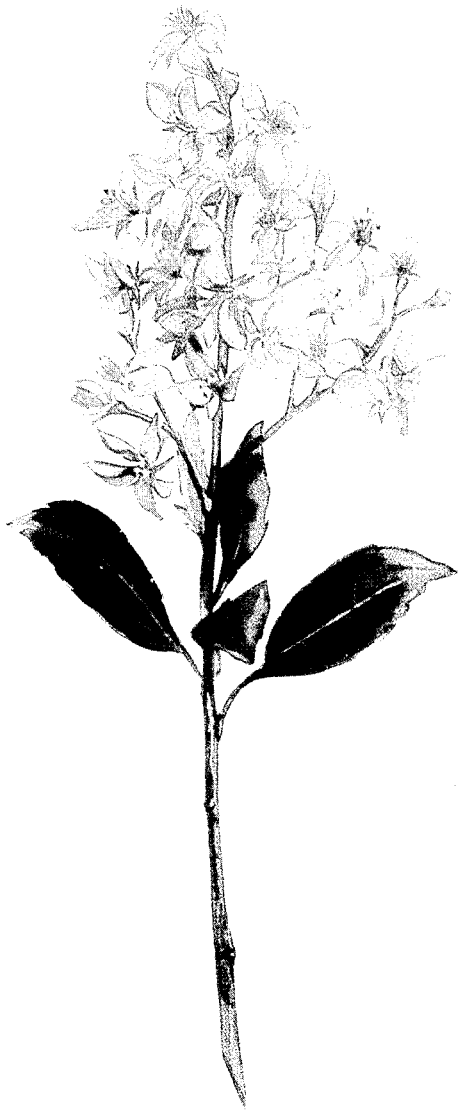
INVENTORS,
HARRY MARKEN
WILLIAM MARKEN
BY Rummler, Rummler & Snow,
ATTORNEYS.

Patented Oct. 14, 1952

Plant Pat. 1,138

UNITED STATES PATENT OFFICE 1,138

RAPHIOLEPIS PLANT

Harry L. Marken and William J. Marken, Morgan Hill, Calif., assignors to Leonard Coates Nurseries, Inc., San Jose, Calif., a corporation of California Application September 10, 1951, Serial No. 245,804

1 Claim. (Cl. 47—60)

Our new discovery relates to a new and distinct variety of Raphiolepis plant of the family Rosaceae, originating as a mutation of the well-known parent variety *Raphiolepis indica rosea* and is characterized as to novelty by its habits of growth, and its coloring of both foliage and blooms as compared with the parent.

Among popular evergreen ornamental shrubs, those belonging to the genus Raphiolepis are well known on the Pacific Coast and in other temperate regions of the United States. *Raphiolepis indica,* unpatented, was introduced into cultivation by the English horticulturists in the early 1800's. This species is usually three to four feet high, has white or pinkish flowers, and elongate leaves which are acute or acuminate at the apex and crenate-serrate on the margins.

The *Raphiolepis indica rosea,* unpatented, the parent of the hereindescribed variety, originated as a seedling in a nursery in San Jose, California, having flowers of a better pink than previously known *Raphiolepis indica* and was propagated vegetatively and introduced to the public in 1924.

The present variety was first observed by us in a large group of seedlings growing in certain propagating grounds at Morgan Hill, California. These seedlings were from seeds collected from plants of *Raphiolepis indica rosea* and sown by us in February 1934. When the seedlings first came into bloom as nursery stock in 1937, the plants bore white flowers, a few produced the pinkish blossoms of the variety *rosea,* while one plant was outstanding because of the intense crimson shade of its flowers.

The new plant was carefully tended, and in 1939 was set out in a private garden in Morgan Hill where it could be tested under normal garden conditions. Experimental tests in propagation by cuttings and grafting were carried on through several generations and adherence to the original flower color has been established.

The accompanying illustration shows the approximate shape of its panicle and its distinctive coloring.

The following is a detailed description of our new variety:

Name: Raphiolepis.
Family: Rosaceae.
Parentage: Mutation of *Raphiolepis indica rosea.*

It has been reproduced asexually from cuttings and grafting since 1938.

Flower: Blooms profusely in April to May and sparsely in the fall.
- *Size.*—Medium. Individual flower about ¾ in. in diameter.
- *Borne.*—In terminal panicles 2½ in. to 5 in. long.
- *Petalage.*—Number—5; form—obovate.
- *Color.*—Deep alizarin crimson. Base lighter shade.
- *Discoloration.*—None.
- *Appearance.*—Satiny.
- Affected by hot weather.
- *Fragrant.*—Yes.
- *Lasting quality.*—On plant—lasts well. As a cut flower—good.

Bud:
- *Length.*—About ¼ inch.
- *Form.*—Longer than broad and somewhat pointed.
- *Color.*—When sepals first divide—green to crimson. When petals begin to unfurl—alizarin crimson.

Sepals: Hooded over bud and stand up.
- *Shape.*—Triangular spear.
- *Tenacity.*—Persistent.

Calyx:
- *Shape.*—Funnel.
- *Color.*—Blotched with crimson.
- *Length.*—About ¼ in.
- *Aspect.*—Tomentose.

Peduncle: Length, very short. Slightly hairy.

Plant:
- *Form.*—Bush (evergreen).
- *Shape.*—30 inches high x 60 inches broad.
- *Growth.*—Slow but vigorous and branching.

Foliage:
- *Quantity.*—Abundant.
- *Size of blade.*—1½ to 2 inches. Alternate on stem.
- Petiole approximately ½ inch.
- *Texture.*—Smooth.
- *Color.*—Upper side—dark green when mature, young growth reddish. Under side—lighter green.
- *Shape.*—Obovate to oblong lanceolate, acute, with margins entire for about one-half of length and serrate toward tip.

Genital organs:

*Stamens*—Length ⅜ inches; number—12 to 20. Color: Anthers—yellow. Filaments—white, turning to a deep crimson as flower ages.

*Arrangment.*—Perigynous.

*Pollen.*—Color—yellow.

*Styles.*—Number—2 to 3; length each ¼ inch.

*Ovaries.*—Inferior.

Fruit:

*Fertile.*—Yes.

*Shape.*—Subglobose. About ¼ to ⅓ inch in diameter.

*Color at maturity.*—Bluish-black.

This new variety of plant at maturity is more compact and smaller than *R. indica* and *R. indica rosea* and slower growing. A distinct difference from the parent plant is in the coloring of the foliage, especially in the new growth which is more reddish and the coloring of the flowers which is much more intense. At the height of its bloom, this new shrub is a mass of beautiful crimson panicles. When the individual flower opens, the color is deepest at the apex of the petals, the anthers are deep yellow and the filaments are white. As the flower ages, the petals become light in color and the filaments turn to a deep crimson. Thus at different stages during the entire life of the plant it presents a pleasing array of color combinations.

The characteristic color of the flowers is identified by reference to the Horticultural Colour Chart, issued by The British Colour Council and The Royal Horticultural Society, volume 1, page 22 as being Crimson 22/1–3.

Having thus disclosed our invention, we claim:

A new and distinct variety of Raphiolepis plant, substantially as herein shown and described, characterized particularly by the distinctive and unique coloring of the flowers.

HARRY L. MARKEN.
WILLIAM J. MARKEN.

No references cited.